United States Patent
Ferrari et al.

(10) Patent No.: US 9,758,454 B2
(45) Date of Patent: Sep. 12, 2017

(54) PROCESS FOR HYDROGENATING DICHLOROISOPROPYL ETHER

(71) Applicant: Dow Global Technologies LLC, Midland, MI (US)

(72) Inventors: Daniela Ferrari, Rosharon, TX (US); Brien A. Stears, Friendswood, TX (US); Yu Liu, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/326,523

(22) PCT Filed: Sep. 9, 2015

(86) PCT No.: PCT/US2015/049066
§ 371 (c)(1),
(2) Date: Jan. 16, 2017

(87) PCT Pub. No.: WO2016/044009
PCT Pub. Date: Mar. 24, 2016

(65) Prior Publication Data
US 2017/0204028 A1    Jul. 20, 2017

Related U.S. Application Data

(60) Provisional application No. 62/051,079, filed on Sep. 16, 2014.

(51) Int. Cl.
| | | |
|---|---|---|
| *C07C 17/361* | (2006.01) | |
| *B01J 23/46* | (2006.01) | |
| *C07C 19/01* | (2006.01) | |
| *C07C 29/10* | (2006.01) | |
| *C07C 31/34* | (2006.01) | |
| *B01J 21/18* | (2006.01) | |
| *B01J 23/889* | (2006.01) | |
| *B01J 35/00* | (2006.01) | |
| *B01J 21/08* | (2006.01) | |
| *B01J 23/80* | (2006.01) | |
| *B01J 23/745* | (2006.01) | |
| *B01J 23/78* | (2006.01) | |

(52) U.S. Cl.
CPC ............. *C07C 17/361* (2013.01); *B01J 21/08* (2013.01); *B01J 21/18* (2013.01); *B01J 23/462* (2013.01); *B01J 23/745* (2013.01); *B01J 23/78* (2013.01); *B01J 23/80* (2013.01); *B01J 23/8892* (2013.01); *B01J 35/0006* (2013.01); *C07C 19/01* (2013.01); *C07C 29/10* (2013.01); *C07C 31/34* (2013.01)

(58) Field of Classification Search
CPC ....... C07C 17/361; C07C 19/01; C07C 29/10; C07C 31/34; B01J 23/462; B01J 21/18; B01J 23/8892; B01J 21/08; B01J 23/80; B01J 23/745; B01J 23/78
See application file for complete search history.

(56) References Cited

U.S. PATENT DOCUMENTS

| | | |
|---|---|---|
| 3,723,544 A | 3/1973 | Roberts, Jr. |
| 4,298,758 A | 11/1981 | Cook et al. |
| 5,401,894 A | 3/1995 | Brasier et al. |

FOREIGN PATENT DOCUMENTS

| | | | |
|---|---|---|---|
| EP | 0287007 | * | 10/1988 |
| EP | 287007 A2 | | 10/1988 |

OTHER PUBLICATIONS

PCT/US2015/049086, International Search Report and Written Opinion dated Dec. 14, 2015.
PCT/US2015/049086, International Preliminary Report on Patentability dated Mar. 21, 2017.

* cited by examiner

*Primary Examiner* — Jafar Parsa

(57) ABSTRACT

Convert dichloroisopropyl ether into a halogenated derivative by contacting the dichloroisopropyl ether with a source of hydrogen and a select heterogeneous hydrogenation catalyst under process conditions selected from a combination of a temperature within a range of from 50 degrees centigrade (° C.) to 350° C., a pressure within a range of from atmospheric pressure (0.1 megapascals) to 1000 pounds per square inch (6.9 MPa), a liquid feed volume flow to catalyst mass ratio between 0.5 and 10 L/Kg*h and a volume hydrogen/volume liquid ratio between 100 and 5000 ml gas/ml liquid. The halogenated derivative is at least one of 1-chloro-2-propanol and 1,2-dichloropropane 1, and glycerin monochlorohydrin.

3 Claims, No Drawings

PROCESS FOR HYDROGENATING DICHLOROISOPROPYL ETHER

The present application claims the benefit of U.S. Provisional Application No. 62/051,079, filed on Sep. 16, 2014.

This invention relates generally to hydrogenation of dichloroisopropyl ether (DCIPE) using a heterogeneous catalyst.

DCIPE is a byproduct of a process for producing propylene oxide using chlorohydrin as a starting material. It represents a significant fraction of what skilled artisans refer to as a propylene dichloride (PDC) bottoms stream from propylene oxide production. The PDC bottoms stream has substantially no commercial value and is typically combusted in a Catoxid™ unit to recover hydrochloric acid (HCl). A desire exists to recover at least a portion of three carbon atom ($C_3$) compounds from the PDC bottoms stream so as to reduce loss of carbon value and load on the Catoxid unit. Illustrative C3 compounds include chlorohydrins, isopropyl ether (IPE), chloropropane, propane and propylene.

U.S. Pat. No. 5,401,894 (Brasier et al.) relates to a process for converting a halogenated organic feedstock to produce a stream of hydrocarbonaceous products that have a very low concentration of halogenated organic compounds and an aqueous stream that contains hydrogen halide. The process involves treating the feedstock in a hydrogenation reaction zone to provide a resulting effluent stream that is contacted with sponge oil, cooled and partially condensed. The resulting cooled stream is introduced into a vapor-liquid separator to produce a hydrogen-rich gaseous recycle stream and a liquid stream containing hydrocarbon compounds, hydrogen halide compounds, possible trace quantities of halogenated organic compounds and the sponge oil. In one embodiment, the halogenated feedstock contains less than 500 parts per million (ppm) of water or water precursors (e.g. oxygenated compounds such as alcohols, aldehydes, epoxides, ketones, phenols and ethers which, when subjected to hydrogenation conditions, are converted to hydrogenated compounds and water). Feedstock options include fractionation bottoms from the purification column in epichlorohydrin production and halogenated ethers.

U.S. Pat. No. 3,723,544 (Roberts, Jr.) teaches a process for ether cleavage of DCIPE to convert it into propylene dichloride and propylene chlorohydrin by adding a catalytic amount of zinc chloride, aluminum chloride or ferric chloride to the DCIPE to form a mixture, heating the mixture in an atmosphere of hydrogen chloride and recovering the products.

European Patent Application (EP) 287007 (Eifler) discloses cleaving aliphatic ethers that have at least one halogen in a beta-position to the oxygen atom by reacting them with an acid halide in the presence of a Lewis acid catalyst to produce the corresponding ester and an alkyl halide.

U.S. Pat. No. 4,298,758 (Cook et al.) presents teachings about reacting dichloropropyl ethers with a carboxylic acid and an alkali metal salt thereof (e.g. acetic acid and sodium acetate). The by-product sodium chloride is insoluble in the acetic acid and easily separated from the reaction mixture. Resulting diesters can be hydrolyzed to their respective glycols.

In some aspects, this invention is a process for converting dichloroisopropyl ether into a halogenated derivative that comprises contacting the dichloroisopropyl ether with a source of hydrogen and a heterogeneous hydrogenation catalyst selected from a group consisting of a ruthenium on carbon catalyst, a copper/chromium/manganese/barium catalyst, a copper/calcium supported on silica catalyst and a copper/zinc catalyst under process conditions selected from a combination of a temperature within a range of from 50 degrees centigrade (° C.) to 350° C., a pressure within a range of from atmospheric pressure 0.1 MPa) to 1000 pounds per square inch (6.9 MPa), a liquid feed volume flow to catalyst mass ratio between 0.5 and 10 L/Kg*h and a volume hydrogen/volume liquid ratio between 100 and 5000 ml gas/ml liquid, the halogenated derivative at least one of 1-chloro-2-propanol and 1,2-dichloropropane, and glycerin monochlorohydrin.

The above process involves combining several process parameters, notably temperature, pressure, liquid feed volume flow to catalyst mass ratio as well as a volume hydrogen/volume liquid ratio as well as choice of catalyst.

The temperature is from 50° C. to 350° C., preferably from 100° C. to 300° C. and more preferably from 150° C. to 250° C. The pressure is from one atmosphere 0.1 MPa) to 1000 pounds per square inch (psi) (6.9 MPa), preferably from 10 psi (0.069 megapascal (MPa) to 200 psi (1.38 MPa), more preferably from 10 psi (0.069 MPa) to 20 psi (0.138 MPa). The liquid feed volume flow to catalyst mass ratio lies within a range of from 0.5 liters per kilogram*hour (L/Kg*h) and 10 L/Kg*h, preferably from 1 L/Kg*h to 8 L/Kg*h and more preferably 8 from 1.4 L/Kg*h to 5 L/Kg*h. The volume hydrogen/volume liquid ratio if from 100 milliliters (ml) gas/ml liquid and 5000 ml gas/ml liquid, preferably from 350 ml gas/ml liquid to 3500 ml gas/ml liquid and more preferably from 600 ml gas/ml liquid to 2700 ml gas/ml liquid. In some aspects, one may minimize reactor plugging by operating at least one of a temperature of no more than 300° C. and a pressure of no more than 200 psi (1.38 MPa).

The heterogeneous hydrogenation catalyst can be supported or unsupported. Suitable hydrogenation metals are selected from Groups VIB and VIII of The Periodic Table of the Elements. A preferred catalyst active component is a metal selected from a group consisting of palladium, ruthenium, platinum, rhodium, iridium, copper, chromium, manganese, zinc, molybdenum, nickel, iron, and tungsten. The catalyst is preferably a supported catalyst that employs a support material selected from a group consisting of carbon, silica, alumina, and mixtures thereof. The hydrogenation catalyst can further comprise a promoter chosen from Groups I and II of The Periodic Table of the Elements such as elements selected from a group consisting of lithium, sodium, potassium, rubidium, cesium, magnesium, calcium, strontium and barium. Preferred catalysts are heterogeneous catalysts selected from a group consisting of a ruthenium on carbon catalyst, a copper/chromium/manganese/barium catalyst, a copper/calcium supported on silica catalyst and a copper/zinc catalyst.

The process of this invention has utility in that it converts a significant portion of a typical PCD bottoms stream, a stream that is, as noted above, typically combusted or burned. The process of this invention converts that DCIPE to halogenated derivatives that have commercial use as feedstocks for various chemical processes.

A typical PCD bottoms stream has the following composition in percent by weight (wt %), based on total bottoms stream weight: PO-propionaldehyde-acetone=0.43 wt %; propylene dichloride=30.35 wt %; epichlorohydrin=4.50 wt %; dichloropropanol=10.4 wt %; DCIPE=53.4 wt % and 0.92 wt % impurities.

A preferred process yields no water. In a process that yields an amount of hydrochloric acid (HCl), the presence of water leads to corrosion of process hardware, especially hardware fabricated from steel. Two such processes are as follows: hydrogenate one mole DCIPE (($ClCH_2CHCH_3$)$_2$O) with one mole of gaseous hydrogen ($H_2$) to yield a mixture of 1-chloropropane ($ClCH_2CH_2CH_3$) and chlorohydrin ($ClCH_2CH(OH)CH_3$); and hydrogenate one mole of DCIPE with two moles of $H_2$ to yield a mixture of isopropyl ether or IPE (($CH_3CHCH_3$)$_2$O) and hydrochloric acid (HCl).

A lesser preferred process produces some water, with hydrogenation of one mole of DCIE using four moles of $H_2$ yielding a mixture of two moles of propane, two moles of HCl and one mole of water; and hydrogenation of one mole of DCIPE with two moles of $H_2$ yielding a mixture of two moles of propane, two moles of HCl and one mole of water.

EXAMPLE 1

Perform catalyst testing in a glass-lined ¼ inch (6.35 millimeter (mm)) reactor placed in an oven. Use a Teledyne ISCO pump for liquid feed to the reactor and use mass flow controllers for hydrogen and nitrogen feeds. Use 0.2 grams (g) to 0.3 g of catalyst and hold the catalyst in place using quartz chips. Purge the reactor to remove oxygen, then reduce the catalyst under flowing hydrogen (10 standard cubic centimeters per minute (sccm) flow rate) at 350° C. and atmospheric pressure for two hours (hr). Heat the reactor to a desired initial temperature that varies with the catalyst as shown in Table 1 below, pressure the reactor to 30 pounds per square inch (206.8 pascals (Pa)) and then start the liquid feed flow. Typical reaction conditions at such a pressure are temperatures of 100° C., 150° C., 200° C., 250° C. and 300° C. with a feed of 10 sccm of hydrogen and 0.45 millimeters per minute (ml/min) of a DCIPE feedstream (99.7 wt % DCIPE and 0.3 wt % 2,3-dichloro-2-propanol). Additional reaction condition sets include a hydrogen feed of 20 sccm and a DCIPE flow rate of either 0.45 ml/min or 0.90 ml/min. See Table 1 below for catalyst test results in terms of liquid product composition in terms of propionaldehyde (PA), acetone (Ac), 1-chloropropane (1-CP), 1-chloro-2-propanol (CPOH), 1,2-dichloropropane (DCP), and IPE using the temperature, $H_2$ flow and DCIPE flow also shown in Table 1.

Catalyst (Cat) A (NobleMax 410™, Clariant) contains 3 wt % ruthenium, 92 wt % active carbon in granule form and 5 wt % water, all wt % being based upon total catalyst weight (Clariant), in an amount of 0.153 g. Cat B (G-99 B-0, Clariant) contains 36.5±1.0 wt % copper, 32±1.0 wt % chromium, 2.3±0.3 wt % manganese, 2.0±0.2 wt % barium and has a surface area of 35.0±10.0 m²/g in an amount of 0.2993 g. Cat C (Cu0860, BASF) contains 50.0 wt %-70.0 wt % copper oxide, 10.0 wt %-30.0 wt % calcium oxide, 10.0 wt %-30.0 wt % silica, 0.0 wt %-10.0 wt % palygorskite (mg($Al_{0.5-1}Fe_{0-0.5}$)$Si_4$(OH)O10.4$H_2$O) and has a surface area of 60 m²/g and a density of 1.11 g/cm³ in an amount of 0.1897 g. Cat D (G-132A, Clariant) contains 30.0±3.0 wt % copper oxide, 60.0±3.0 wt % zinc oxide and 8.0±1.0 wt % alumina in an amount of 0.2211 g.

TABLE 1

| Cat | T (° C.) | $H_2$ Flow (sccm) | DCIPE Flow (ml/hr) | DCIPE Conv (%) | Liquid Product (wt %) | | | | | |
|---|---|---|---|---|---|---|---|---|---|---|
| | | | | | PA | Ac | 1-CP | CPOH | DCP | IPE |
| A | 250 | 20 | 0.45 | 68.1 | 14.7 | 0.0 | 2.5 | 76.1 | 4.5 | 2.2 |
| A | 250 | 20 | 0.9 | 45.8 | 2.7 | 12.8 | 4.3 | 64.4 | 11.6 | 4.2 |
| B | 150 | 10 | 0.45 | 7.3 | 8.2 | 0.9 | 0.0 | 90.9 | 0.0 | 0.0 |
| B | 200 | 10 | 0.45 | 4.7 | 5.4 | 1.6 | 0.0 | 81.5 | 11.5 | 0.0 |
| B | 250 | 10 | 0.45 | 30.8 | 4.7 | 4.5 | 0.0 | 49.3 | 38.7 | 2.8 |
| B | 300 | 10 | 0.45 | 47.1 | 6.0 | 5.5 | 0.0 | 28.9 | 56.9 | 2.7 |
| B | 200 | 20 | 0.45 | 0.5 | 7.5 | 5.2 | 0.0 | 74.7 | 12.6 | 0.0 |
| B | 200 | 20 | 0.9 | 0.7 | 6.9 | 37.9 | 0.0 | 42.6 | 12.6 | 0.0 |
| C | 300 | 10 | 0.45 | 53.8 | 8.2 | 4.7 | 1.3 | 35.4 | 48.8 | 1.6 |
| C | 250 | 20 | 0.45 | 3.5 | 11.5 | 5.7 | 0.0 | 66.3 | 16.5 | 0.0 |
| C | 250 | 20 | 0.9 | 0.2 | 9.9 | 5.5 | 0.0 | 63.4 | 21.2 | 0.0 |
| C | 250 | 10 | 0.45 | 11.4 | 9.3 | 5.0 | 0.0 | 63.8 | 21.9 | 0.0 |
| C | 250 | 10 | 0.45 | 10.1 | 8.7 | 4.8 | 0.0 | 66.4 | 20.1 | 0.0 |
| C | 250 | 10 | 0.45 | 9.4 | 9.9 | 5.9 | 0.0 | 63.5 | 20.7 | 0.0 |
| D | 100 | 10 | 0.45 | 9.2 | 7.3 | 2.4 | 0.0 | 90.3 | 0.0 | 0.0 |
| D | 150 | 10 | 0.45 | 31.0 | 5.5 | 2.4 | 0.0 | 72.9 | 15.5 | 3.7 |
| D | 200 | 10 | 0.45 | 41.4 | 6.9 | 4.9 | 1.9 | 59.7 | 24.4 | 2.2 |
| D | 200 | 20 | 0.45 | 15.7 | 5.8 | 1.8 | 0.0 | 80.8 | 11.6 | 0.0 |
| D | 200 | 10 | 0.9 | 4.1 | 11.7 | 4.8 | 0.0 | 73.3 | 10.3 | 0.0 |
| D | 250 | 10 | 0.45 | 43.3 | 5.3 | 6.3 | 1.8 | 40.3 | 44.2 | 2.1 |
| D | 250 | 20 | 0.45 | 8.2 | 8.4 | 4.0 | 0.0 | 68.0 | 19.6 | 0.0 |
| D | 250 | 10 | 0.9 | 3.3 | 12.1 | 5.6 | 0.0 | 61.8 | 20.5 | 0.0 |

The data in Table 1 show that 1-chloro-2-propanol and 1,2-dichloropropane are the principal products obtained during hydrogenation using the catalysts and conditions shown in and preceding Table 1.

EXAMPLE 2

Replicate Example 1 with changes. As one change, use a PCD bottoms stream as a liquid feedstream that contains PO-propionaldehyde-acetone=0.43 wt %; propylene dichloride=30.35 wt %; epichlorohydrin=4.50 wt %; dichloropropanol=10.4 wt %; DCIPE=53.4 wt %; and impurities=0.93 wt %. As a second change, use a feed flow of 0.45 ml/hr for all runs. As a third change, alter the catalyst amounts to 0.1182 g for Cat A, 0.3005 g for Cat B, 0.1923 g for Cat C and 0.2213 g for Cat D.

TABLE 2

| Cat | T (° C.) | H$_2$ Flow (sccm) | DCIPE Conv (%) | Liquid Product (wt %) | | | | | | | | |
|---|---|---|---|---|---|---|---|---|---|---|---|---|
| | | | | PA | Ac | 1-CP | CPOH | DCP | IPE | 2-GMCH | 1,3-DCOH | 2,3-DCOH |
| A | 200 | 10 | 17.2 | 4.6 | 0.5 | 0.8 | 5.4 | 39.8 | 1.4 | 31.1 | 3.1 | 13.3 |
| A | 250 | 10 | 27.3 | 4.6 | 0.9 | 0.0 | 4.1 | 34.7 | 1.2 | 37.9 | 4.7 | 11.9 |
| A | 300 | 10 | 44.0 | 4.2 | 1.3 | 0.0 | 5.1 | 31.3 | 1.0 | 41.9 | 4.4 | 10.8 |
| A | 250 | 20 | 29.5 | 2.6 | 0.3 | 0.0 | 7.9 | 35.8 | 1.3 | 29.3 | 6.2 | 16.6 |
| B | 150 | 10 | 31.2 | 1.3 | 0.1 | 0.0 | 9.0 | 34.0 | 1.1 | 24.8 | 12.2 | 17.5 |
| B | 200 | 10 | 30.4 | 1.4 | 0.3 | 0.0 | 7.0 | 25.8 | 1.3 | 44.2 | 8.2 | 11.8 |
| B | 250 | 10 | 43.0 | 1.8 | 0.8 | 0.0 | 5.8 | 19.4 | 1.2 | 59.0 | 5.6 | 6.4 |
| C | 150 | 10 | 58.4 | 1.9 | 0.1 | 0.0 | 6.9 | 37.1 | 1.3 | 23.5 | 9.5 | 19.7 |
| C | 200 | 10 | 39.7 | 1.7 | 0.1 | 0.0 | 7.0 | 32.9 | 1.4 | 26.7 | 8.6 | 21.6 |
| C | 250 | 10 | 48.9 | 5.0 | 0.9 | 0.0 | 2.7 | 31.8 | 1.1 | 41.4 | 5.8 | 11.3 |
| D | 150 | 10 | 39.1 | 3.4 | 0.2 | 0.0 | 4.6 | 37.4 | 1.4 | 30.3 | 7.6 | 15.1 |
| D | 200 | 10 | 23.8 | 3.6 | 0.5 | 0.0 | 3.9 | 35.2 | 1.4 | 33.9 | 7.3 | 14.2 |
| D | 250 | 10 | 46.6 | 3.9 | 1.5 | 0.0 | 6.7 | 29.1 | 1.0 | 43.5 | 5.2 | 9.1 |

The data in Table 2 show that the catalysts are active in converting DCIPE to a product stream that contains 1,2-dichloropropane and 2-GMCH as principal products.

What is claimed is:

1. A process for converting dichloroisopropyl ether into a halogenated derivative that comprises contacting the dichloroisopropyl ether with a source of hydrogen and a heterogeneous hydrogenation catalyst selected from a group consisting of a ruthenium on carbon catalyst, a copper/chromium/manganese/barium catalyst, a copper/calcium supported on silica catalyst and a copper/zinc catalyst under process conditions selected from a combination of a temperature within a range of from 50 degrees centigrade (° C.) to 350° C., a pressure within a range of from atmospheric pressure (0.1 megapascals) to 1000 pounds per square inch (6.9 MPa), a liquid feed volume flow to catalyst mass ratio between 0.5 and 10 L/Kg*h and a volume hydrogen/volume liquid ratio between 100 and 5000 ml gas/ml liquid, the halogenated derivative at least one of 1-chloro-2-propanol and 1,2-dichloropropane, and glycerin monochlorohydrin.

2. The process of claim 1, wherein the combination includes at least one of a temperature of from 100° C. to 300° C., a pressure of from 10 psi (0.069 megapascal (MPa) to 200 psi (1.38 MPa, a liquid feed volume flow to catalyst mass ratio within a range of from 1 L/Kg*h to 8 L/Kg*h, and a volume hydrogen/volume liquid ratio of from 350 ml gas/ml liquid to 3500 ml gas/ml liquid.

3. The process of claim 1, wherein the combination includes at least one of a temperature of from 150° C. to 250° C., a pressure of from 10 psi (0.069 MPa) to 20 psi (0.138 MPa), a liquid feed volume flow to catalyst mass ratio within a range of from 1.4 L/Kg*h to 5 L/Kg*h, and a volume hydrogen/volume liquid ratio of from 600 ml gas/ml liquid to 2700 ml gas/ml liquid.

* * * * *